United States Patent
Hu et al.

(10) Patent No.: US 11,837,026 B1
(45) Date of Patent: Dec. 5, 2023

(54) METHOD, APPARATUS, DEVICE, AND STORAGE MEDIA FOR EARLY WARNING UNSAFE BEHAVIOR IN DRILLING OPERATION

(71) Applicant: CHINA UNIVERSITY OF PETROLEUM—BEIJING, Beijing (CN)

(72) Inventors: Jinqiu Hu, Beijing (CN); Laibin Zhang, Beijing (CN); Chuangang Chen, Beijing (CN); Mingyuan Wu, Beijing (CN)

(73) Assignee: CHINA UNIVERSITY OF PETROLEUM-BEIJING CHINA, Beijing (CN)

( * ) Notice: Subject to any disclaimer, the term of this patent is extended or adjusted under 35 U.S.C. 154(b) by 0 days.

(21) Appl. No.: 18/297,206

(22) Filed: Apr. 7, 2023

(30) Foreign Application Priority Data

Jan. 5, 2023 (CN) .......................... 202310011174.7

(51) Int. Cl.
| | | |
|---|---|---|
| G06V 40/20 | (2022.01) | |
| G06T 7/246 | (2017.01) | |
| G06V 40/18 | (2022.01) | |
| G06F 3/01 | (2006.01) | |
| E21B 41/00 | (2006.01) | |
| G06F 3/0484 | (2022.01) | |

(52) U.S. Cl.
CPC .......... *G06V 40/20* (2022.01); *E21B 41/0021* (2013.01); *G06F 3/013* (2013.01); *G06F 3/0484* (2013.01); *G06T 7/248* (2017.01); *G06V 40/197* (2022.01); *G06T 2207/20081* (2013.01)

(58) Field of Classification Search
CPC .. G06V 40/20; G06V 40/197; E21B 41/0021; G06F 3/013; G06F 3/0484; G06T 7/248; G06T 2207/20081
See application file for complete search history.

(56) References Cited

U.S. PATENT DOCUMENTS

2023/0290182 A1* 9/2023 Hu ....................... G06V 10/774
382/103

FOREIGN PATENT DOCUMENTS

| CN | 106251065 A | * 12/2016 |
|---|---|---|
| CN | 107562202 A | * 1/2018 |

* cited by examiner

*Primary Examiner* — Abhishek Sarma
(74) *Attorney, Agent, or Firm* — Maier & Maier, PLLC (57) ABSTRACT

A method, an apparatus, a device, and a storage medium for early warning of an unsafe behavior in drilling operation. The method includes obtaining eye movement data of a drilling operator in a sensitive area, obtaining a value of an eye movement parameter of the drilling operator about a drilling operation station according to the eye movement data, inputting the value of the eye movement parameter to an early warning model to obtain an operation type of the drilling operator in working on the drilling operation station, and transmitting an early warning message to a preset terminal when the operation type is a preset type. The method achieves a rapid and accurate identification of unsafe behaviors of drilling operators, thereby avoiding the occurrence of drilling accidents.

16 Claims, 5 Drawing Sheets

METHOD, APPARATUS, DEVICE, AND STORAGE MEDIA FOR EARLY WARNING UNSAFE BEHAVIOR IN DRILLING OPERATION

CROSS-REFERENCE TO RELATED APPLICATIONS

This application claims priority to Chinese Patent Application No. 202310011174.7, filed on Jan. 5, 2023, which is hereby incorporated by reference in its entirety.

TECHNICAL FIELD

The present application relates to the field of drilling technologies, and in particular, to a method, an apparatus, a device, and a storage medium for early warning an unsafe behavior in drilling operation.

BACKGROUND

Oil and gas drilling is a concealed underground project with multi-type, multi-process, interchange, and continuous operation. Drilling operation is one of the high-risk fields in the oil and gas industry, and the accident rate caused by drilling operation is usually higher that other fields in the industry.

At present, a main development direction of the drilling operation is the adoption of equipment and facilities with higher robotization and intelligentialize, strengthening safety management, and increasing safety training. However, due to the limitation of technological development, the operation on instruments and screen monitoring by people on drilling operation stations cannot be completely replaced by machines. Due to the complexity and diversity of human physiology and psychological activities during the operation, human factors are the most important reason for frequent drilling accidents.

In the analysis of drilling accidents caused by human factors, behaviors that tend to cause wrong behaviors are easy to be ignored. Therefore, how to monitor and early warn an unsafe behavior of a drilling operator to reduce the occurrence of a drilling accident is the problem to be solved at present.

SUMMARY

The present application provides a method, an apparatus, a device, and a storage medium for early warning an unsafe behavior in drilling operation. By obtaining eye movement data of a drilling operator in a sensitive area, obtaining a value of an eye movement parameter of the drilling operator about a drilling operation station according to the eye movement data, and identifying an operation type of the drilling operator according to the value of the eye movement parameter, the monitoring and early warning of unsafe behaviors of drilling operators can be achieved, thereby reducing the occurrence of drilling accidents.

In a first aspect, the present application provides a method for early warning an unsafe behavior in drilling operation, including:
  obtaining eye movement data of a drilling operator in a sensitive area, where the sensitive area is an area in a drilling operation station, and the sensitive area is determined according to an eye movement hot spot map of a previous drilling operator and includes a parameter screen region, an instrument region, a drilling site region, and an operation region;
  obtaining a value of an eye movement parameter of the drilling operator about the drilling operation station according to the eye movement data, where the eye movement parameter includes at least one of a total number of gazing points in the sensitive area, a total time-length of gazing points in the sensitive area, a total scanning time-length in the sensitive area, a total scanning distance in the sensitive area, or an average pupil diameter;
  inputting the value of the eye movement parameter to an early warning model to obtain an operation type of the drilling operator in working on the drilling operation station, where the early warning model is obtained by training according to values of the eye movement parameter of the previous drilling operator and operation types; and
  transmitting an early warning message to a preset terminal when the operation type is a preset type, where the early warning message is configured to indicate that the drilling operator has an unsafe behavior.

Optionally, before obtaining the eye movement data of the drilling operator in the sensitive area, the method further includes:
  obtaining the eye movement hot spot map of the previous drilling operator and a target device in the drilling operation station corresponding to the eye movement hot spot map; and
  determining a sensitive region corresponding to the target device according to a type of the target device and the eye movement hot spot map.

Optionally, determining the sensitive region corresponding to the target device according to the type of the target device and the eye movement hot spot map includes:
  determining a candidate region according to a red region in the eye movement hot spot map;
  determining a target region according to the type of the target device, and judging whether the candidate region covers the target region;
  in a situation that the candidate region covers the target region, using the candidate region as the sensitive region;
  in a situation that the candidate region does not cover the target region, determining the candidate region according to the red region and a single-color region around the red region in the eye movement hot spot map to make the candidate region cover the target region, and using the candidate region as the sensitive region, where the red region has a heat degree greater than the heat degree of the single-color region.

Optionally, in a situation that the sensitive region is the parameter screen region or the drilling site region, and the target device has a type of a display screen or an observation window, determining the target region according to the type of the target device includes:
  determining a display region of the display screen or the observation window according to a display content of the display screen or the observation window;
  using the display region as the target region;
  where the display screen is configured to display a parameter, and different parameters correspond to different display regions, the observation window is configured to display a drilling scene, and drilling scenes of different types correspond to different display contents in the observation window, where the display contents are a drilling device associated with the drilling scenes of different types.

Optionally, in a situation that the sensitive region is the instrument region or the operation region, and the target device has a type of an instrument or an operation component, determining the target region according to the type of the target device includes:

determining a contour of the target device according to the type of the target device, and using the contour as the target region;

where using the candidate region as the sensitive region includes:

judging whether a contour of the candidate region matches with the contour of the target region;

in a situation that the contour of the candidate region matches with the contour of the target region, determining that the candidate region is used as the sensitive region;

in a situation that the contour of the candidate region does not match with the contour of the target region, adjusting the contour of the candidate region until it matches with the contour of the target region, and determining that the adjusted candidate region is used as the sensitive region.

Optionally, the eye movement data includes at least one of gazing-point distribution information, scanning space-time path information, gazing-point time-length information, or pupil information.

The obtaining the value of the eye movement parameter of the drilling operator about the drilling operation station according to the eye movement data includes at least one of the followings:

obtaining the number of gazing points in each sensitive region according to the gazing-point distribution information, and a total number of gazing points in the sensitive area according to the number of gazing points in each sensitive region; or obtaining a time-length of each gazing point in each sensitive region according to the gazing-point time-length information, and a total time-length of gazing points in the sensitive area according to the time-length of each gazing point in each sensitive region; or obtaining a scanning distance and/or scanning time-length in each sensitive region according to the scanning space-time path information, and a total scanning distance and/or scanning time-length in the sensitive area according to the scanning distance and/or scanning time-length in each sensitive region; or obtaining an average pupil diameter according to the pupil information obtained in different periods.

Optionally, the early warning model is a LightGBM (Light Gradient Boosting Machine) model optimized based on TPE (Tree-structured Parzen Estimator).

In a second aspect, the present application provides an apparatus for early warning an unsafe behavior in drilling operation, including:

an obtaining module, configured to obtain eye movement data of a drilling operator in a sensitive area, where the sensitive area is an area in a drilling operation station, and the sensitive area is determined according to an eye movement hot spot map of a previous drilling operator and includes a parameter screen region, an instrument region, a drilling site region, and an operation region; and the obtaining module is further configured to obtain a value of an eye movement parameter of the drilling operator about the drilling operation station according to the eye movement data, where the eye movement parameter includes at least one of a total number of gazing points in the sensitive area, a total time-length of gazing points in the sensitive area, a total scanning time-length in the sensitive area, a total scanning distance in the sensitive area, or an average pupil diameter;

a processing module, configured to input the value of the eye movement parameter to an early warning model to obtain an operation type of the drilling operator in working on the drilling operation station, where the early warning model is obtained by training according to values of the eye movement parameter of the previous drilling operator and operation types; and a transmitting module, configured to transmit an early warning message to a preset terminal when the operation type is a preset type, where the early warning message is configured to indicate that the drilling operator has an unsafe behavior.

Optionally, the obtaining module is further configured to obtain the eye movement hot spot map of the previous drilling operator and a target device in the drilling operation station corresponding to the eye movement hot spot map.

The apparatus for early warning the unsafe behavior in drilling operation further includes a determination module.

The determination module is configured to determine a sensitive region corresponding to the target device according to a type of the target device and the eye movement hot spot map.

Optionally, the determination module is specifically configured to determine a candidate region according to a red region in the eye movement hot spot map, and determine a target region according to the type of the target device.

The apparatus for early warning the unsafe behavior in drilling operation further includes a judgment module.

The judgment module is configured to judge whether the candidate region covers the target region.

The determination module is specifically configured to use the candidate region as the sensitive region when the candidate region covers the target region, determine the candidate region according to the red region and a single-color region around the red region in the eye movement hot spot map when the candidate region does not cover the target region to make the candidate region cover the target region, and use the candidate region as the sensitive region, where the red region has a heat degree greater than the heat degree of the single-color region.

Optionally, if the sensitive region is the parameter screen region or the drilling site region, and the target device has a type of a display screen or an observation window, the determination module is specifically configured to determine a display region of the display screen or the observation window according to a display content of the display screen or the observation window, and use the display region as the target region. The display screen is configured to display a parameter, and different parameters correspond to different display regions. The observation window is configured to display a drilling scene, and drilling scenes of different types correspond to different display contents in the observation window, where the display contents are a drilling device associated with the drilling scenes of different types.

Optionally, if the sensitive region is the instrument region or the operation region, and the target device has a type of an instrument or an operation component, the determination module is specifically configured to determine a contour of the target device according to the type of the target device, and use the contour as the target region.

The judgment module is specifically configured to judge whether a contour of the candidate region matches with the contour of the target region.

The determination module is specifically configured to determine that the candidate region is used as the sensitive region when the contour of the candidate region matches with the contour of the target region.

The determination module is specifically configured to adjust the contour of the candidate region until it matches with the contour of the target region when the contour of the candidate region does not match with the contour of the target region, and determine that the adjusted candidate region is used as the sensitive region.

Optionally, the eye movement data includes at least one of gazing-point distribution information, scanning space-time path information, gazing-point time-length information, or pupil information.

The obtaining module is specifically configured to obtain the number of gazing points in each sensitive region according to the gazing-point distribution information, and a total number of gazing points in the sensitive area according to the number of gazing points in each sensitive region; or obtain a time-length of each gazing point in each sensitive region according to the gazing-point time-length information, and a total time-length of gazing points in the sensitive area according to the time-length of each gazing point in each sensitive region; or obtain a scanning distance and/or scanning time-length in each sensitive region according to the scanning space-time path information, and a total scanning distance and/or scanning time-length in the sensitive area according to the scanning distance and/or scanning time-length in each sensitive region; or obtain an average pupil diameter according to pupil information obtained in different periods.

Optionally, the early warning model is a LightGBM (Light Gradient Boosting Machine) model optimized based on TPE (Tree-structured Parzen Estimator).

In a third aspect, the present application provides a device for early warning an unsafe behavior in drilling operation, including: a memory and a processor;

where the memory stores a computer execution instruction;

the processor executes the computer execution instruction stored in the memory to implement the method for early warning the unsafe behavior in drilling operation as described in the first aspect and various possible embodiments in the first aspect.

In a fourth aspect, the present application provides a computer-readable storage medium, and computer-readable storage medium stores a computer program. The computer program is executed by a processor to implement the method for early warning the unsafe behavior in drilling operation as described in the first aspect and various possible embodiments in the first aspect.

By obtaining eye movement data of a drilling operator in a sensitive area, obtaining a value of an eye movement parameter of the drilling operator about a drilling operation station according to the eye movement data, inputting the value of the eye movement parameter to an early warning model to obtain an operation type of the drilling operator in working on the drilling operation station, and transmitting an early warning message to a preset terminal when the operation type is a preset type, the method for early warning the unsafe behavior in drilling operation according to the present application achieves a rapid and accurate identification of unsafe behaviors of drilling operators, thereby avoiding the occurrence of drilling accidents, and at the same time, reducing the effect of irrelevant and wrong eye movement data on the accuracy rate of identifying operation types of drilling operators by determining sensitive regions by the eye movement hot spot map.

BRIEF DESCRIPTION OF DRAWINGS

The drawings herein are incorporated into the specification and form a part of the specification, show embodiments in accordance with the present application, and are used together with the specification to explain the principle of the present application.

The specific embodiments of the present application have been shown through the above drawings, which will be described in more detail below. These drawings and descriptions are not intended to limit the scope of the concept of the present application in any manner, but to explain the concept of the present application to those skilled in the art by referring to specific embodiments.

DETAILED DESCRIPTION OF THE EMBODIMENTS

In order to make the purpose, technical solution, and advantages of the present application clearer, the technical solution in the present application will be described clearly and completely in combination with the drawings of the present application. Apparently, the described embodiments are a part of rather than all embodiments of the present application. Based on embodiments of the present application, all other embodiments obtained by persons of ordinary skill in the art without creative work fall within the protection scope of the present application.

The terms "first", "second", "third", "fourth", etc. (if exists) in the description, claims, and the above drawings of the present application are used to distinguish similar objects, and are not used to describe a specific order or sequence. It should be understood that the data used in this way can be interchanged in an appropriate case, so that the embodiments of the present application described herein can be implemented in order other than those illustrated or described herein.

First, the terms involved in the present application are explained.

Eye movement data: data obtained from an eye movement behavior of a subject, which is generally obtained through an eye tracking technology.

Eye tracking technology: it is a technology in which information such as a gazing position, a scanning path, and a gazing time-length of eyes of a subject is tracked and recorded by an eye movement data sensor. The use of the eye tracking technology can not only record eye movement information of a drilling operator, but also track attention distribution of the drilling operator, so as to achieve the identification of fatigue operation and an unskilled behavior of the drilling operator.

Eye movement hot spot map: it is mainly used to reflect the browsing and gazing situation of a subject. Eye movement hot spot map is also called eye movement heat map or eye movement heat region map. The hot spot map can show the attention distribution of a subject. In general, in the eye movement hot spot map, a red region represents a region with the most concentrated browsing and gazing, and a yellow region and a green region represent regions with less gazing, respectively.

Sensitive area: an area where a drilling operator needs to focus on during drilling operation, that is, an area where important units are located in drilling operation, usually including regions where an instrument, a valve, a drilling bit, a device operation station, etc. of a drilling device are located.

Oil and gas drilling is a concealed underground project with multi-type, multi-process, interchange, and continuous operation. Drilling operation is one of the high-risk fields in the oil and gas industry, and the accident rate caused by drilling operation is usually higher than other fields in the industry.

At present, a main development direction of the drilling operation is the adoption of equipment and facilities with higher robotization and intelligentialize, strengthening safety management, and increasing safety training. However, due to the limitation of technological development, the role of man in the drilling operation cannot be completely replaced by machines. Due to the complexity and diversity of human physiological and psychological activities during the operation, human factors are the most important reason for frequent drilling accidents.

In the analysis of drilling accidents caused by human factors, with regard to a wrong behavior that has been formed, an operator can be timely reminded to make a corresponding correction by means of inspection by an inspector, and the combination of a monitoring camera and intelligent identification, etc.

However, behaviors that tend to cause wrong behaviors (for example, unsafe behaviors such as fatigue operation and unskilled work, etc. that may be more likely to cause wrong behaviors) are often difficult to be detected because accidents had not yet occurred at that time. In actual production operation, if unsafe behaviors such as fatigue operation and unskilled operation are not strictly controlled, these unsafe behaviors will further cause significant property losses and casualties. Therefore, how to monitor and early warn an unsafe behavior of a drilling operator to reduce the occurrence of a drilling accident is the problem to be solved at present.

Figure 1:
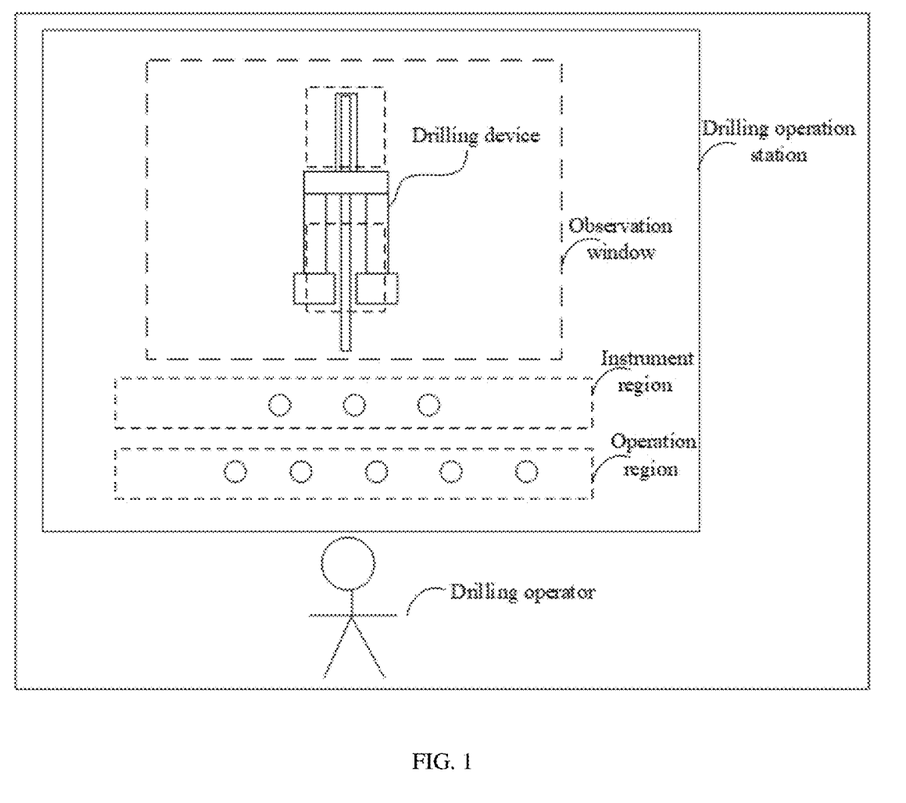
FIG. 1 is a schematic diagram of a scene where a drilling operator performs drilling operation according to the present application.

In view of the above problem, the present application provides a method for early warning an unsafe behavior in drilling operation. FIG. 1 is a schematic diagram of a scene where a drilling operator performs drilling operation according to the present application. As shown in FIG. 1, a drilling operation station includes an observation window from which a drilling site can be seen, an instrument region that shows a current operation parameter, and an operation region for an operator to operate. A drilling operator needs to observe the drilling site and instrument region, and perform operation on an operation component in the operation region to finish current drilling operation. During the drilling operation, an eye movement data sensor will track and record eye movement data of the drilling operator. The eye movement data sensor can be provided on working glasses worn by the drilling operator during the drilling operation, or other wearable devices such as a helmet, a hat, etc. worn by the drilling operator during the drilling operation.

The following is a detailed description of the technical solutions of the present application and how the technical solutions of the present application solve the above technical problem with specific embodiments. The following specific embodiments can be combined with each other. The same or similar concepts or processes may not be repeated in some embodiments. Embodiments of the present application will be described below in conjunction with the drawings.

Figure 2:
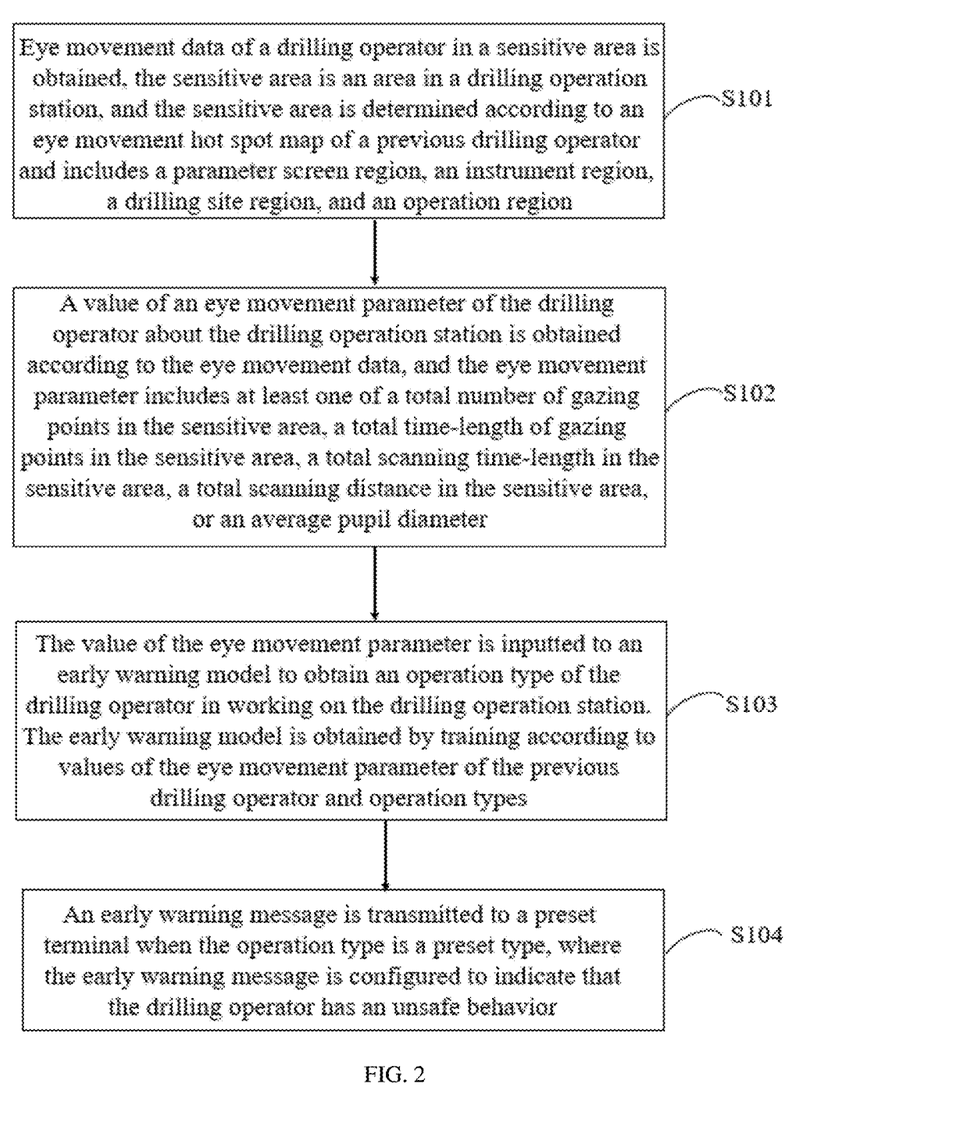
FIG. 2 is a first flow chart of a method for early warning an unsafe behavior in drilling operation according to the present application.

FIG. 2 is a first flow chart of a method for early warning an unsafe behavior in drilling operation according to the present application. This embodiment can be applied, for example, to a server, and as shown in FIG. 2, a method for early warning an unsafe behavior in drilling operation shown in this embodiment includes:

S101: eye movement data of a drilling operator in a sensitive area is obtained, the sensitive area is an area in a drilling operation station, and the sensitive area is determined according to an eye movement hot spot map of a previous drilling operator and includes a parameter screen region, an instrument region, a drilling site region, and an operation region.

The eye movement data in the sensitive area refers to data collected in the sensitive area by an eye movement data sensor. After the eye movement data of the drilling operator is recorded by the eye movement data sensor, the eye movement data of the drilling operator in the sensitive area is obtained.

It is understandable that the drilling operator needs to observe a drilling site from an observation window and the instrument region in the drilling operation station, and operate an operation component in the operation region. It can be seen that the sensitive area includes multiple regions, and the multiple regions are those in the drilling operation station and in the drilling site, for example, part region of the drilling site seen from the observation window, part of the instrument region, and part of the operation region. That is, the sensitive area includes a parameter screen region, an instrument region, a drilling site region, and an operation region.

S102: a value of an eye movement parameter of the drilling operator about the drilling operation station is obtained according to the eye movement data, and the eye movement parameter includes at least one of a total number of gazing points in the sensitive area, a total time-length of gazing points in the sensitive area, a total scanning time-length in the sensitive area, a total scanning distance in the sensitive area, or an average pupil diameter.

After the eye movement data of the sensitive area is obtained, the value of the eye movement parameter of the drilling operator about the drilling operation station can be obtained according to the eye movement data.

In the existing technology, eye movement parameters are in various types, and appropriate eye movement parameters are needed to be selected from them. The eye movement parameter in this step includes at least one of a total number of gazing points in the sensitive area, a total time-length of gazing points in the sensitive area, a total scanning time-length in the sensitive area, a total scanning distance in the sensitive area, or an average pupil diameter, which can accurately reflect operation types of the drilling operator. The total number or total time-length is the summation with respect to the corresponding parameter for multiple sensitive regions.

S103: the value of the eye movement parameter is inputted to an early warning model to obtain an operation type of the drilling operator in working on the drilling operation station. The early warning model is obtained by training according to values of the eye movement parameter of the previous drilling operator and operation types.

The early warning model is a model that is trained in advance by values of the eye movement parameter of the previous drilling operator and operation types. This model can output an operation type of the drilling operator. The early warning model can be, for example, a LightGBM (Light Gradient Boosting Machine) model optimized based on TPE (Tree-structured Parzen Estimator).

The operation types of the drilling operator for example can include normal operation, fatigued operation, and unskilled operation. After the eye movement data is input to the early warning model, the model will output an operation type of the drilling operator.

In this embodiment, the attention of the drilling operator on each sensitive region is converted to the attention of the drilling operator on the whole drilling operation station by the obtaining of the value of the eye movement parameter and the processing of the early warning model, so as to better feedback whether the drilling operator has a potential unsafe behavior when the drilling operator operates on the drilling operation station.

S104: an early warning message is transmitted to a preset terminal when the operation type is a preset type, where the early warning message is configured to indicate that the drilling operator has an unsafe behavior.

The preset type, for example, can be fatigued operation or unskilled operation. The preset terminal, for example, can be either a terminal device corresponding to a security officer or a preset terminal device. The unsafe behavior may include, for example, that the drilling operator is currently in a fatigued state or that the drilling operator is unable to skillfully operate on the drilling operation station.

For example, when the outputted operation type is "fatigued operation", an early warning message indicating that the drilling operator is currently in a fatigued status is transmitted to a terminal device of a safety officer.

By obtaining eye movement data of a drilling operator in a sensitive area; obtaining a value of an eye movement parameter of the drilling operator about a drilling operation station according to the eye movement data; inputting the value of the eye movement parameter to an early warning model to obtain an operation type of the drilling operator in working on the drilling operation station; and transmitting an early warning message to a present terminal when the operation type is a preset type, the method for early warning the unsafe behavior in drilling operation according to this embodiment achieves rapid and accurate identification of unsafe behaviors of drilling operators, thereby avoiding the occurrence of drilling accidents, and at the same time reducing the effect of irrelevant and wrong eye movement data on the accuracy rate of identifying operation types of drilling operators by determining sensitive regions by the eye movement hot spot map.

Figure 3:
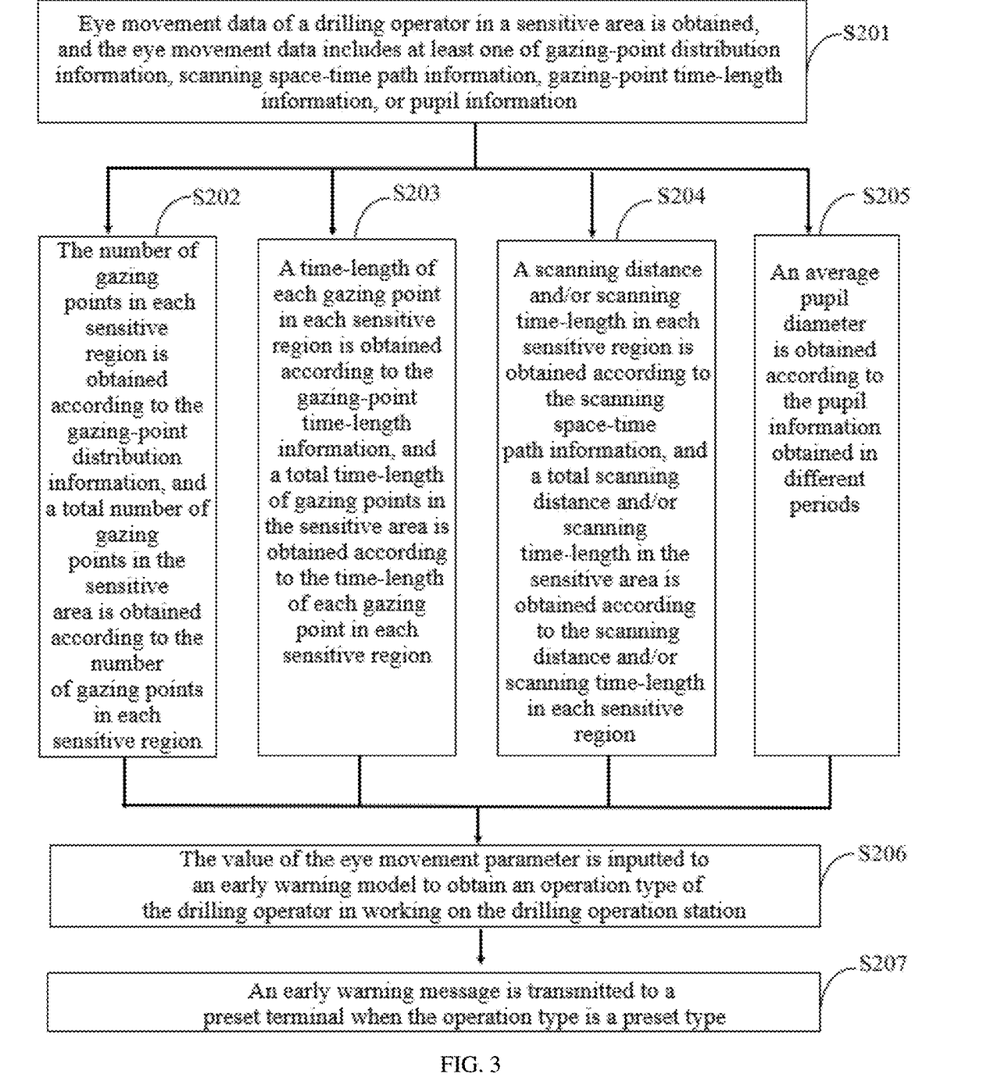
FIG. 3 is a second flow chart of a method for early warning an unsafe behavior in drilling operation according to the present application.

FIG. 3 is a second flow chart of a method for early warning an unsafe behavior in drilling operation according to the present application. As shown in FIG. 3, this embodiment is the description of a method for early warning an unsafe behavior in drilling operation in detail based on the embodiment of FIG. 1. A method for early warning an unsafe behavior in drilling operation shown in this embodiment include:

S201: eye movement data of a drilling operator in a sensitive area is obtained, and the eye movement data includes at least one of gazing-point distribution information, scanning space-time path information, gazing-point time-length information, or pupil information.

The gazing-point distribution information refers to the distribution of gazing points of the drilling operator in the sensitive area, and for example can include the number of gazing points in each sensitive region. The scanning space-time path information refers to a time-length and a distance for the drilling operator to scan in each sensitive region when the drilling operator works on the drilling operator station. The gazing-point time-length information refers to a time-length of each gazing point in each sensitive region gazed by the drilling operator. The pupil information refers to information about the drilling operator's pupil during drilling operation, such as a size of the pupil, a maximum diameter of the pupil, etc.

The way of obtaining the eye movement data in this step is similar to that in step S101 above, and will not be repeated here.

S202: the number of gazing points in each sensitive region is obtained according to the gazing-point distribution information, and a total number of gazing points in the sensitive area is obtained according to the number of gazing points in each sensitive region.

The number of gazing points in each sensitive region can be determined according to the gazing-point distribution information of the drilling operator in the sensitive area, and then the total number of gazing points in the sensitive area can be obtained according to the number of gazing points in each sensitive region. For example, the total number of gazing points in the sensitive area $F_{pn}$ can be obtained by the following formula (1):

$$F_{pn}=F_{pn1}+F_{pn2}+\ldots+F_{pni} \quad i=1,2,3,4, \tag{1}$$

where $F_{pni}$ is the number of gazing points in the it h sensitive region. That is, the total number of gazing points in the sensitive area is obtained by adding the numbers of gazing points in respective sensitive regions together.

S203: a time-length of each gazing point in each sensitive region is obtained according to the gazing-point time-length information, and a total time-length of gazing points in the sensitive area is obtained according to the time-length of each gazing point in each sensitive region.

The gazing-point time-length information includes a time-length of each gazing point in each sensitive region gazed by the drilling operator.

A total time-length of gazing points in each sensitive region can be obtained according to the time-length of each gazing point in each sensitive region gazed by the drilling operator, and then the total time-length of gazing points in the sensitive area can be obtained according to the total time-length of gazing points in each sensitive region. For example, the total time-length of gazing points in the sensitive area $F_t$ can be obtained by the following formula (2):

$$F_t = F_{t1} + F_{t2} + \ldots + F_{ti}, i=1,2,3,4, \quad (2)$$

where $F_{t1}$ is the total time-length of gazing points in the $i^{th}$ sensitive region. That is, the total time-length of gazing points in the sensitive area is obtained by adding the total time-length of gazing points in respective sensitive regions together.

S204: a scanning distance and/or scanning time-length in each sensitive region is obtained according to the scanning space-time path information, and a total scanning distance and/or scanning time-length in the sensitive area is obtained according to the scanning distance and/or scanning time-length in each sensitive region.

The scanning space-time path information includes a time-length and/or distance for the drilling operator to scan in each sensitive region.

The total scanning distance and/or scanning time-length in the sensitive area can be obtained according to the scanning time-length and/or scanning distance in each sensitive region. For example, the total scanning time-length in the sensitive area $S_t$ and the total scanning distance in sensitive areas $S_{lt}$ can be obtained by the following formulas (3) and (4):

$$S_t = S_{t1} + S_{t2} + \ldots + S_{ti}, i=1,2,3,4, \quad (3)$$

where $S_{ti}$ is the scanning time-length in the $i^{th}$ sensitive region. That is, the total scanning time-length in the sensitive area can be obtained by adding scanning time-lengths in respective sensitive regions together.

$$S_{lt} = S_{lt1} + S_{lt2} + \ldots + S_{lti}, i=1,2,3,4, \quad (4)$$

where $S_{lti}$ is the scanning distance in the $i^{th}$ sensitive region. That is, the total scanning distance in the sensitive area can be obtained by adding scanning distances in respective sensitive regions together.

S205: an average pupil diameter is obtained according to the pupil information obtained in different periods.

The pupil information is collected according to a preset period, and for example, the present period may be 20 milliseconds. The pupil information includes the drilling operator's pupil diameter. The pupil diameter can reflect the operation type of the drilling operator. It is understandable that when the drilling operator is in fatigued operation, the pupil diameter is relatively small, which is because when people are tired, their pupils will become smaller accordingly.

This step can obtain the average pupil diameter of the drilling operator during drilling operation according to the pupil information of different periods. For example, the average pupil diameter $P_d$ can be obtained by the following formula (5):

$$P_d = P_{d1} + P_{d2} + \ldots + P_{di}, i=1,2,3,4, \quad (5)$$

where $P_{di}$ is the pupil diameter of the drilling operator collected in the $i^{th}$ time.

S206: the value of the eye movement parameter is inputted to an early warning model to obtain an operation type of the drilling operator in working on the drilling operation station.

S207: an early warning message is transmitted to a preset terminal when the operation type is a preset type.

Step S206 and step S207 are similar to the above step S103 and step S104, and will not be repeated here.

The method for early warning an unsafe behavior of a drilling operation according to this embodiment can obtain the operation type of the drilling operator according to multi-type eye movement parameter values, thereby improving the accuracy of early warning. At the same time, since the eye movement parameter includes at least one of a total number of gazing points in the sensitive area, a total time-length of gazing points in the sensitive area, a total scanning time-length in the sensitive area, a total scanning distance in the sensitive area, or an average pupil diameter, that is representative parameters are used for early warning, the effect of too many eye movement parameters and improper selection on the implementation efficiency of the early warning model can be avoided.

Figure 4:
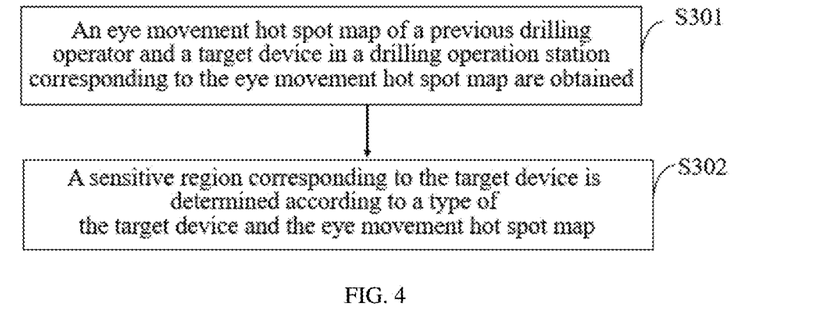
FIG. 4 is a third flow chart of a method for early warning an unsafe behavior in drilling operation according to the present application.

FIG. 4 is a third flow chart of a method for early warning an unsafe behavior in drilling operation according to an embodiment of the present application. It is understandable that, a sensitive region of a sensitive area needs to be determined before eye movement data of a drilling operator in the sensitive area is obtained. As shown in FIG. 4, this embodiment is a detail description of a process of determining a sensitive region of a sensitive area before eye movement data of a drilling operator in the sensitive area is obtained based on the embodiments of FIG. 2 and FIG. 3. A method for early warning an unsafe behavior in drilling operation shown in this embodiment include:

S301: an eye movement hot spot map of a previous drilling operator and a target device in a drilling operation station corresponding to the eye movement hot spot map are obtained.

The eye movement hot spot map is an eye movement hot spot map of the drilling operation station, which may reflect a corresponding eye movement behavior of the drilling operator when operating on the drilling operation station. It is understandable that when the drilling operator operates on the drilling operation station, his work contents are relatively single, such as operating an operation component or viewing an image of a specific region on a display screen. Therefore, regions on which the drilling operator focuses are also relatively fixed.

The target device refers to an instrument on the drilling operation station, such as wellhead equipment, a hydraulic tong, etc., on a drilling site, a status indicator displayed on the screen display, an operation handle, a switch button, a power ammeter, a weight indicator, etc. In this step, the eye movement hot spot map of the previous drilling operator on the drilling operation station and the target device in the drilling operation station are obtained.

S302: a sensitive region corresponding to the target device is determined according to a type of the target device and the eye movement hot spot map.

The drilling operation station includes various types of devices, such as a power ammeter which belongs to the instrument category, an operation handle and switch button which belong to the operation component category, and a hydraulic tong which belongs to the drilling site category. After the target device and eye movement hot spot map are obtained, the sensitive region corresponding to the target device can be determined according to the type of the target device and the eye movement hot spot map.

It is understandable that the determined sensitive regions are different with regard to target devices of different types. For example, a sensitive region corresponding to a target device of the instrument category is a region that covers the target device, or a sensitive region corresponding to a target device of the operation component category is a preset region including the target device. The present application does not make special restrictions on the specific implementation method of determining a sensitive region corresponding to a target device.

The method for early warning the unsafe behavior in drilling operation according to this embodiment determines sensitive regions corresponding to target devices according to the eye movement hot spot map and the types of the target devices in the drilling operation station, thereby improving the accuracy of determining sensitive regions and ensuring that effective eye movement data can be obtained.

Figure 5:
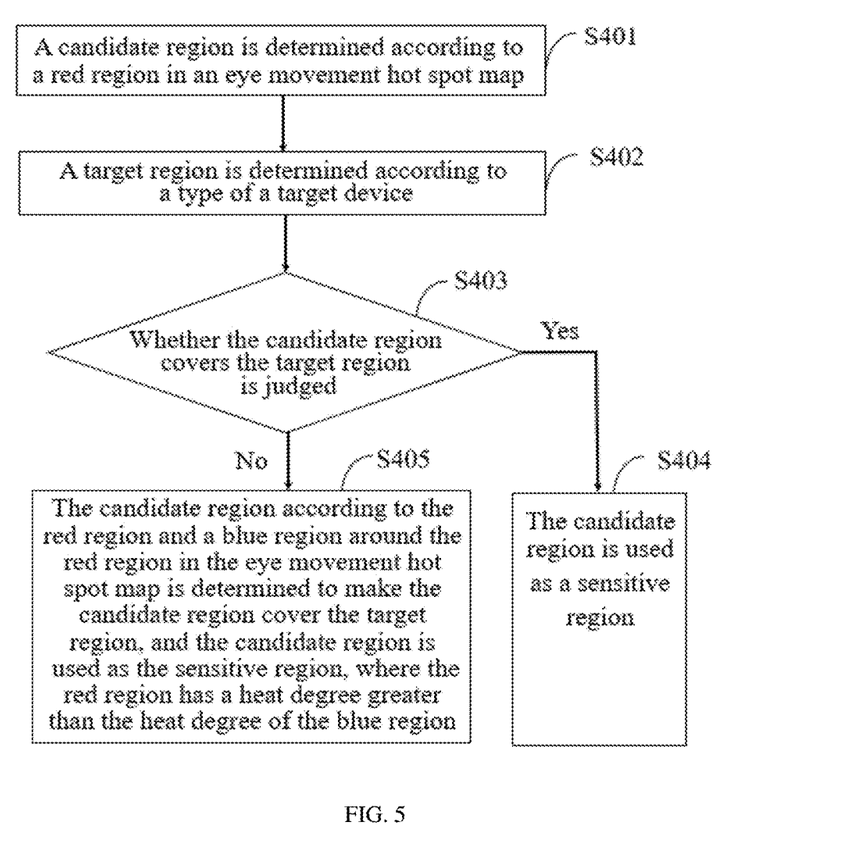
FIG. 5 is a fourth flow chart of a method for early warning an unsafe behavior in drilling operation according to the present application.

FIG. 5 is a fourth flow chart of a method for early warning an unsafe behavior in drilling operation according to an embodiment of the present application. As shown in FIG. 5, this embodiment is a detail description of determining a sensitive region corresponding to a target device according to the type of the target device and an eye movement hot spot map based on the embodiment of FIG. 4. A method for early warning an unsafe behavior in drilling operation shown in this embodiment includes:

S401: a candidate region is determined according to a red region in an eye movement hot spot map.

The eye movement hot spot map can visually show regions and ranges where lines of sight focus on. The eye movement hot spot map is a visual radiation intensity distribution image formed by a specific functional relationship between the gazing situation by a drilling operator in drilling operation and a corresponding regional parameter in the image. The presentation effect of the map is determined by time-lengths of gazing points and corresponding positions of the gazing points, which are allocated by pixel points. In the eye movement hot spot map, different colors represent time-lengths for which the drilling operator gazes at corresponding regions. In general, red indicates that the drilling operator has a longer gazing time in a corresponding region, while blue indicates the opposite.

In order to avoid the effect of irrelevant, incorrect and other eye movement data on the accuracy rate of identifying operation types, a candidate region can be determined according to a red region in an eye movement hot spot map, that is, the candidate region can be determined according to a region at which a previous drilling operator gazed for a long time.

S402: a target region is determined according to a type of a target device.

The target region refers to a region corresponding to the target device. Target devices of different types correspond to different target regions. There are various types of devices on the drilling operation station. A target region corresponding to the type of a target device can be determined according to the type of the target device.

Optionally, if a sensitive region is a parameter screen region or a drilling site region, and a target device has a type of a display screen or an observation window, a specific implementation manner of determining a target region according to the type of the target device is determining a display region of the display screen or the observation window according to a display content of the display screen or the observation window, and using the display region as the target region.

A corresponding parameter is displayed on the display screen. The display region on the display screen can be determined according to a parametric dial displayed on the display screen. For example, if the display screen shows a drilling parameter or a weight indicator dial for a drilling well control simulation system, the display region on the display screen is determined as a region corresponding to the drilling parameter or a region corresponding to the weight indicator dial. It is understandable that different parameters correspond to different display regions.

A drilling scene is displayed in the observation window, and a display region in the observation window can be determined according to a display content of the observation window. The displayed content is a drilling device associated with the type of the drilling scene. For example, if a wellhead device is displayed in the observation window, the type of the drilling scene is determined to be a wellhead scene, and the display region in the observation window is a region corresponding to the wellhead advice. It is understandable that drilling scenes of different types correspond to different display contents in the observation window.

In this step, target regions determined by different display contents are different, thereby improving the accuracy and diversity of the determination of target regions.

Optionally, if a sensitive region is an instrument region or an operation region, and a target device has a type of an instrument or an operation component, a specific implementation manner of determining a target region according to the type of the target device is determining a contour of the target device according to the type of the target device, and using the contour as the target region.

When a target device has a type of an instrument panel or an operating component, the contour of the target device includes a contour corresponding to the instrument panel and a contour corresponding to the operation component. At this point, the contour of the target device can be used as a target region. That is, a region corresponding to the target device is the target region.

S403: whether the candidate region covers the target region is judged; if yes, step S404 is executed; if no, step S405 is executed.

After the candidate region and the target region are determined, there is a need to determine whether the candidate region covers the target region. If yes, the candidate region is determined as a sensitive region, and if no, the candidate region is determined by both the red region and a single-color region around the red region in the eye movement hot spot map. It is understandable that the purpose of judgment is to make the target region corresponding to the target device covered, so as to obtain the sensitive area, thereby ensuring that the scope of the sensitive area is accurate and relevant eye movement data will not be omitted.

S404: the candidate region is used as a sensitive region.

Specifically, if a sensitive region is the instrument region or the operation region, a target device has a type of an instrument or an operation component, a method to determine a target region is determining a contour of the target device according to the type of the target device, using the contour as the target region, and using the candidate region as the sensitive region, including:

judging whether the contour of the candidate region and the contour of the target region are matched with each other; if matched, determining to use the candidate region as the sensitive region; if not matched, adjusting the contour of the candidate region until it matches with the contour of the target region, and determining to use the adjusted candidate region as the sensitive region.

Regarding the judgement of whether the contour of the candidate region and the contour of the target region are matched with each other, for example, it can be judged that whether the shape of the candidate region is the same as the shape of the target region. The purpose is to determine sensitive regions corresponding to some target devices having special contours.

It is understandable that there are some target devices having special shapes on the drilling operation station. For example, instruments are in irregular shapes. For a device with an irregular shape, there is a need to match the contour of the sensitive region with the contour of the irregular-shaped device, so as to facilitate the effective acquisition of the eye movement data.

Therefore, there is a need to determine whether the contour of the candidate region and the contour of the target region are matched with each other, and if matched, the candidate region is determined as the sensitive area, if not matched, the contour of the candidate region needs to be adjusted until it matches with the contour of the target region, and then the adjusted candidate region is used as the sensitive region.

Figure 6:
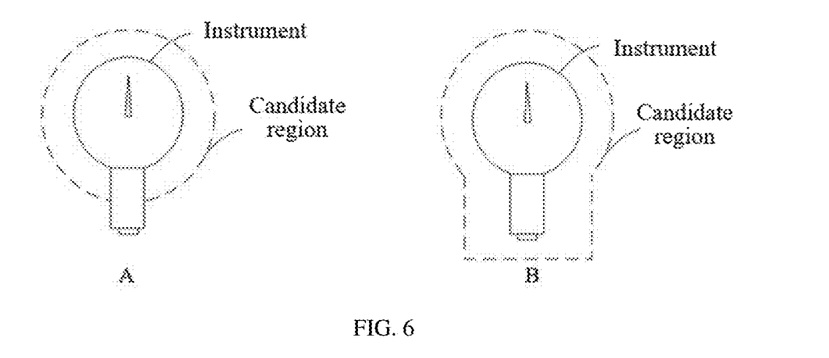
FIG. 6 is a schematic diagram of a candidate region according to the present application.

FIG. 6 is a schematic diagram of a candidate region according to the present embodiment. As shown in FIG. 6A, an instrument has a contour of an irregular shape. At this time, the contour of a candidate region corresponding to the instrument covers the instrument, but does not cover a battery region below the instrument, that is, the contour of the candidate region does not match with the contour of the target device. It is understandable that a drilling operator when working will focus on the instrument and the battery region below the instrument. Therefore, if the candidate region in FIG. 6A is used as the sensitive region for the instrument, there is a defect that a lot of eye movement data about the battery region will be lost.

Therefore, when the contour of the candidate region does not match with the contour of the target device, there is a need to adjust the contour of the candidate region until it matches with the contour of the target region, that is, the contour of the candidate region shown in FIG. 6B. As shown in FIG. 6B, the candidate region covers the region where the instrument is located, and covers the battery region below the instrument. The adjusted candidate region is used as the sensitive region, thereby avoiding the defect of the loss of the eye movement data about the battery region and improving the accuracy and diversity of the determination of the sensitive region.

S405: the candidate region is determined according to the red region and a single-color region around the red region in the eye movement hot spot map, so that the candidate region covers the target region, and the candidate region is used as the sensitive region, where the red region has a heat degree greater than the heat degree of the single-color region. The method for early warning an unsafe behavior in drilling operator according to this embodiment reduces the effect of irrelevant and wrong eye movement data on the accuracy rate of identifying the unsafe behavior of the drilling operator by determining the candidate region according to the red region in the eye movement hot spot map. At the same time, when the candidate region determined according to the red region does not cover the target region, the candidate region is jointly determined according to the red region and the single-color region around the red region in the eye movement hot spot map, thereby improving the accuracy rate of the determined sensitive region and ensuring that effective eye movement data can be obtained.

Figure 7:
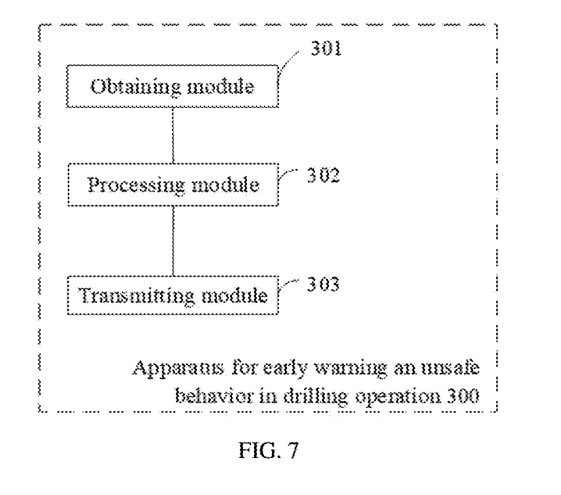
FIG. 7 is a schematic structural diagram of an apparatus for early warning an unsafe behavior in drilling operation according to the present application.

FIG. 7 is a schematic structural diagram of an apparatus for early warning an unsafe behavior in drilling operation according to the present application. As shown in FIG. 7, the present application provides an apparatus for early warning an unsafe behavior in drilling operation. An apparatus for early warning an unsafe behavior in drilling operation 300 includes:

an obtaining module 301, configured to obtain eye movement data of a drilling operator in a sensitive area, where the sensitive area is an area in a drilling operation station, and the sensitive area is determined according to an eye movement hot spot map of a previous drilling operator and includes a parameter screen region, an instrument region, a drilling site region, and an operation region;

the obtaining module 301 is further configured to obtain a value of an eye movement parameter of the drilling operator about the drilling operation station according to the eye movement data, where the eye movement parameter includes at least one of a total number of gazing points in the sensitive area, a total time-length of gazing points in the sensitive area, a total scanning time-length in the sensitive area, a total scanning distance in the sensitive area, or an average pupil diameter;

a processing module 302, configured to input the value of the eye movement parameter to an early warning model to obtain an operation type of the drilling operator in working on the drilling operation station, where the early warning model is obtained by training according to values of the eye movement parameter of the previous drilling operator and operation types; and a transmitting module 303, configured to transmit an early warning message to a preset terminal when the operation type is a preset type, where the early warning message is configured to indicate that the drilling operator has an unsafe behavior.

Optionally, the obtaining module 301 is further configured to obtain the eye movement hot spot map of the previous drilling operator and a target device in the drilling operation station corresponding to the eye movement hot spot map.

The apparatus for early warning the unsafe behavior in drilling operation further includes a determination module 304, and the determination module 304 is configured to determine a sensitive region corresponding to the target device according to a type of the target device and the eye movement hot spot map.

Optionally, the determination module 304 is specifically configured to determine a candidate region according to a red region in the eye movement hot spot map, and determine a target region according to the type of the target device.

The apparatus for early warning the unsafe behavior in drilling operation further includes a judgment module 305, and the judgment module 305 is configured to judge whether the candidate region covers the target region.

The determination module 304 is specifically configured to use the candidate region as the sensitive region when the candidate region covers the target region, determine the candidate region according to the red region and a single-color region around the red region in the eye movement hot spot map when the candidate region does not cover the target region to make the candidate region cover the target region, and use the candidate region as the sensitive region, where the red region has a heat degree greater than the heat degree of the single-color region.

Optionally, if the sensitive region is the parameter screen region or the drilling site region, and the target device has a type of a display screen or an observation window, the determination module 304 is specifically configured to determine a display region of the display screen or the observation window according to a display content of the display screen or the observation window, and use the display region as the target region. The display screen is configured to display a parameter, and different parameters correspond to different display regions. The observation window is configured to display a drilling scene, and drilling scenes of different types correspond to different display contents in the observation window, where the display contents are a drilling device associated with the drilling scenes of different types.

Optionally, if the sensitive region is the instrument region or the operation region, and the target device has a type of an instrument or an operation component, the determination module 304 is specifically configured to determine a contour of the target device according to the type of the target device, and use the contour as the target region.

The judgment module 305 is specifically configured to judge whether a contour of the candidate region matches with the contour of the target region.

The determination module 304 is specifically configured to determine that the candidate region is used as the sensitive region when the contour of the candidate region matches with the contour of the target region.

The determination module 304 is specifically configured to adjust the contour of the candidate region until it matches with the contour of the target region when the contour of the candidate region does not match with the contour of the target region, and determine that the adjusted candidate region is used as the sensitive region.

Optionally, the eye movement data includes at least one of gazing-point distribution information, scanning space-time path information, gazing-point time-length information, or pupil information.

The obtaining module 301 is specifically configured to obtain the number of gazing points in each sensitive region according to the gazing-point distribution information, and a total number of gazing points in the sensitive area according to the number of gazing points in each sensitive region; or     obtain a time-length of each gazing point in each sensitive region according to the gazing-point time-length information, and a total time-length of gazing points in the sensitive area according to the time-length of each gazing point in each sensitive region; or     obtain a scanning distance and/or scanning time-length in each sensitive region according to the scanning space-time path information, and a total scanning distance and/or scanning time-length in the sensitive area according to the scanning distance and/or scanning time-length in each sensitive region; or     obtain an average pupil diameter according to pupil information obtained in different periods.

Optionally, the early warning model is a LightGBM (Light Gradient Boosting Machine) model optimized based on TPE (Tree-structured Parzen Estimator).

Figure 8:
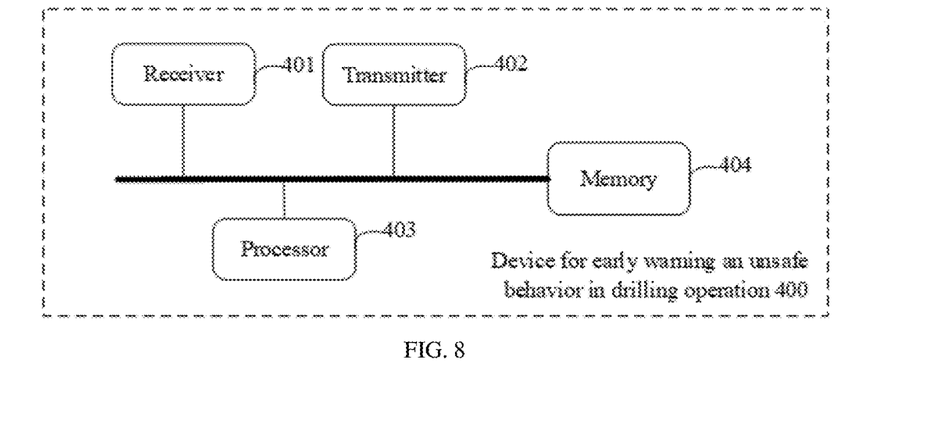
FIG. 8 is a schematic structural diagram of a device for early warning an unsafe behavior in drilling operation according to the present application.

FIG. 8 is a schematic structural diagram of a device for early warning an unsafe behavior in drilling operation according to the present application. As shown in FIG. 8, the present application provides a device for early warning an unsafe behavior in drilling operation. A device for early warning an unsafe behavior in drilling operation 400 includes a receiver 401, a transmitter 402, a processor 403, and a memory 404.

The receiver 401 is configured to receive an instruction and data.

The transmitter 402 is configured to transmit an instruction and data.

The memory 404 is configured to store a computer execution instruction.

The processor 403 is configured to execute the computer execution instruction stored in the memory 404 to implement the steps of the method for early warning the unsafe behavior in drilling operation in the above embodiments. For details, please refer to the relevant description in the embodiments of the method for early warning the unsafe behavior in drilling operation.

Optionally, the memory 404 can be either independent or integrated with the processor 403.

When the memory 404 is provided independently, the electronic device further includes a bus for connecting the memory 404 and the processor 403.

The present application further provides a computer-readable storage medium, and the computer-readable storage medium stores a computer-executed instruction. When the processor executes the computer-executed instruction, a method for early warning an unsafe behavior in drilling operation performed by a device for early warning the unsafe behavior in drilling operation, described as above, can be implemented.

Those skilled in the art can understand that all or some of the steps, systems, and functional modules/units in the apparatus disclosed above can be implemented as software, firmware, hardware, and an appropriate combination thereof. In a hardware implementation, the division between functional modules/units mentioned in the above description does not necessarily correspond to the division of physical components, and for example, a physical component can have multiple functions, or a function or step can be performed by several physical components in cooperation. Some or all physical components can be implemented as software that is executable by a processor such as a central processing unit, a digital signal processor, or a microprocessor, or as hardware, or as an integrated circuit such as a special-purpose integrated circuit. Such software may be distributed on a computer-readable medium, and the computer-readable medium may include a computer storage medium (or non-temporary medium) and a communication medium (or temporary medium). As is known to those skilled in the art, the term "computer storage medium" includes a volatile medium, a non-volatile medium, a removable medium, and a non-removable medium implemented in any method or technology for storing information (such as a computer-readable instruction, a data structure, a program module, or other data). The computer storage medium includes but is not limited to a RAM, a ROM, an EEPROM, a flash memory or other storage technologies, a CD-ROM, a digital multifunction disc (DVD) or other optical disk storage, a magnetic box, a magnetic tape, a magnetic disk storage or other magnetic storage devices, or any other media that can be used to store desired information and can be accessed by a computer. In addition, it is known to those skilled in the art that the communication medium generally includes a computer-readable instruction, a data structure, a program module, or other data in a modulated data signal such as a carrier or other transmission mechanism, and may include any information delivery medium.

Those skilled in the art will easily conceive of other embodiments of the present application after considering the description and implementing the present application disclosed herein. The present application is intended to cover any variant, use or adaptive change of the present application. These variants, uses or adaptive changes follow the general principle of the present application, and include common knowledge or conventional technical means in the technical field that are not disclosed in the present application. The description and the embodiments are only regarded to be exemplary, and the true scope and spirit of the present application are indicated in the appended claims.

What is claimed is:

1. An apparatus for early warning an unsafe behavior in drilling operation, comprising:
an obtaining module configured to obtain eye movement data of a drilling operator in a sensitive area, wherein the sensitive area is an area in a drilling operation station, and the sensitive area is determined according to an eye movement hot spot map of a previous drilling operator and comprises a parameter screen region, an instrument region, a drilling site region, and an operation region;
wherein the obtaining module is further configured to obtain a value of an eye movement parameter of the drilling operator about the drilling operation station according to the eye movement data, wherein the eye movement parameter comprises at least one of a total number of gazing points in the sensitive area, a total time-length of gazing points in the sensitive area, a total scanning time-length in the sensitive area, a total scanning distance in the sensitive area, or an average pupil diameter;
a processing module configured to input the value of the eye movement parameter to an early warning model to obtain an operation type of the drilling operator in working on the drilling operation station, wherein the early warning model is obtained by training according to values of the eye movement parameter of the previous drilling operator and operation types; and
a transmitting module configured to transmit an early warning message to a preset terminal when the operation type is a preset type, wherein the early warning message is configured to indicate that the drilling operator has an unsafe behavior.

2. A method for early warning an unsafe behavior in drilling operation, comprising:
obtaining eye movement data of a drilling operator in a sensitive area, wherein the sensitive area is an area in a drilling operation station, and the sensitive area is determined according to an eye movement hot spot map of a previous drilling operator and comprises a parameter screen region, an instrument region, a drilling site region, and an operation region;
obtaining a value of an eye movement parameter of the drilling operator about the drilling operation station according to the eye movement data, wherein the eye movement parameter comprises at least one of a total number of gazing points in the sensitive area, a total time-length of gazing points in the sensitive area, a total scanning time-length in the sensitive area, a total scanning distance in the sensitive area, or an average pupil diameter;
inputting the value of the eye movement parameter to an early warning model to obtain an operation type of the drilling operator in working on the drilling operation station, wherein the early warning model is obtained by training according to values of the eye movement parameter of the previous drilling operator and operation types; and
transmitting an early warning message to a preset terminal when the operation type is a preset type, wherein the early warning message is configured to indicate that the drilling operator has an unsafe behavior.

3. The method according to claim 2, wherein before obtaining the eye movement data of the drilling operator in the sensitive area, the method further comprises:
obtaining the eye movement hot spot map of the previous drilling operator and a target device in the drilling operation station corresponding to the eye movement hot spot map; and
determining a sensitive region corresponding to the target device according to a type of the target device and the eye movement hot spot map.

4. The method according to claim 3, wherein determining the sensitive region corresponding to the target device according to the type of the target device and the eye movement hot spot map comprises:
determining a candidate region according to a red region in the eye movement hot spot map;
determining a target region according to the type of the target device, and judging whether the candidate region covers the target region;
in a situation that the candidate region covers the target region, using the candidate region as the sensitive region; and
in a situation that the candidate region does not cover the target region, determining the candidate region according to the red region and a single-color region around the red region in the eye movement hot spot map to make the candidate region cover the target region, and using the candidate region as the sensitive region, wherein the red region has a heat degree greater than the heat degree of the single-color region.

5. The method according to claim 4, wherein in a situation that the sensitive region is the parameter screen region or the drilling site region and the target device has a type of a display screen or an observation window, determining the target region according to the type of the target device comprises:
determining a display region of the display screen or the observation window according to a display content of the display screen or the observation window; and
using the display region as the target region;
wherein the display screen is configured to display a parameter, and different parameters correspond to different display regions, the observation window is configured to display a drilling scene, and drilling scenes of different types correspond to different display contents in the observation window, wherein the display contents are a drilling device associated with the drilling scenes of different types.

6. The method according to claim 4, wherein in a situation that the sensitive region is the instrument region or the operation region and the target device has a type of an instrument or an operation component, determining the target region according to the type of the target device comprises:
determining a contour of the target device according to the type of the target device, and using the contour as the target region;
wherein using the candidate region as the sensitive region comprises:
judging whether a contour of the candidate region matches with the contour of the target region;
in a situation that the contour of the candidate region matches with the contour of the target region, determining that the candidate region is used as the sensitive region; and
in a situation that the contour of the candidate region does not match with the contour of the target region, adjusting the contour of the candidate region until it matches with the contour of the target region, and determining that the adjusted candidate region is used as the sensitive region.

7. The method according to claim 3, wherein the eye movement data comprise at least one of gazing-point distribution information, scanning space-time path information, gazing-point time-length information, or pupil information;
wherein obtaining the value of the eye movement parameter of the drilling operator about the drilling operation station according to the eye movement data comprises at least one of the following:
obtaining the number of gazing points in each sensitive region according to the gazing-point distribution information, and a total number of gazing points in the sensitive area according to the number of gazing points in each sensitive region; or
obtaining a time-length of each gazing point in each sensitive region according to the gazing-point time-length information, and a total time-length of gazing points in the sensitive area according to the time-length of each gazing point in each sensitive region; or
obtaining a scanning distance and/or scanning time-length in each sensitive region according to the scanning space-time path information, and a total scanning distance and/or scanning time-length in the sensitive area according to the scanning distance and/or scanning time-length in each sensitive region; or
obtaining an average pupil diameter according to the pupil information obtained in different periods.

8. The method according to claim 2, wherein the early warning model is a LightGBM model optimized based on TPE.

9. A device for early warning an unsafe behavior in drilling operation, comprising a memory and a processor;
wherein the memory stores a computer execution instruction; and
the processor executes the computer execution instruction stored in the memory to implement the method for early warning the unsafe behavior in drilling operation according to claim 2.

10. The device for early warning an unsafe behavior in drilling operation according to claim 9, wherein before the processor obtains the eye movement data of the drilling operator in the sensitive area, the processor further obtains the eye movement hot spot map of the previous drilling operator and a target device in the drilling operation station corresponding to the eye movement hot spot map; and
determines a sensitive region corresponding to the target device according to a type of the target device and the eye movement hot spot map.

11. The device for early warning an unsafe behavior in drilling operation according to claim 10, wherein the processor determines the sensitive region corresponding to the target device according to the type of the target device and the eye movement hot spot map comprising:
determines a candidate region according to a red region in the eye movement hot spot map;
determines a target region according to the type of the target device, and judges whether the candidate region covers the target region;
in a situation that the candidate region covers the target region, the candidate region is used as the sensitive region;
in a situation that the candidate region does not cover the target region, determines the candidate region according to the red region and a single-color region around the red region in the eye movement hot spot map to make the candidate region cover the target region, and the candidate region is used as the sensitive region, wherein the red region has a heat degree greater than the heat degree of the single-color region.

12. The device for early warning an unsafe behavior in drilling operation according to claim 11, wherein in a situation that the sensitive region is the parameter screen region or the drilling site region, and the target device has a type of a display screen or an observation window, the processor determines the target device according to the type of the target device, comprising:
determines a display region of the display screen or the observation window according to a display content of the display screen or the observation window;
uses the display region as the target region;
wherein the display screen is configured to display a parameter, and different parameters correspond to different display regions, the observation window is configured to display a drilling scene, and drilling scenes of different types correspond to different display contents in the observation window, wherein the display contents are a drilling device associated with the drilling scenes of different types.

13. The device for early warning an unsafe behavior in drilling operation according to claim 11, wherein in a situation that the sensitive region is the instrument region or the operation region, and the target device has a type of an instrument or an operation component, the processor determines the target region according to the type of the target device, comprising:
determines a contour of the target device according to the type of the target device, and uses the contour as the target region;
wherein the processor uses the candidate region as the sensitive region comprising:
judges whether a contour of the candidate region matches with the contour of the target region;
in a situation that the contour of the candidate region matches with the contour of the target region, determines that the candidate region is used as the sensitive region;
in a situation that the contour of the candidate region does not match with the contour of the target region, adjusts the contour of the candidate region until it matches with the contour of the target region, and determines that the adjusted candidate region is used as the sensitive region.

14. The device for early warning an unsafe behavior in drilling operation according to claim 10, wherein the eye movement data comprise at least one of gazing-point distribution information, scanning space-time path information, gazing-point time-length information, or pupil information;
wherein the processor obtains the value of the eye movement parameter of the drilling operator about the drilling operation station according to the eye movement data, comprising at least one of the followings:
obtains the number of gazing points in each sensitive region according to the gazing-point distribution information, and a total number of gazing points in the sensitive area according to the number of gazing points in each sensitive region; or
obtains a time-length of each gazing point in each sensitive region according to the gazing-point time-length information, and a total time-length of gazing points in the sensitive area according to the time-length of each gazing point in each sensitive region; or obtains a scanning distance and/or scanning time-length in each sensitive region according to the scanning space-time path information, and a total scanning distance and/or scanning time-length in the sensitive area according to the scanning distance and/or scanning time-length in each sensitive region; or obtains an average pupil diameter according to the pupil information obtained in different periods.

15. The device for early warning an unsafe behavior in drilling operation according to claim 9, wherein the early warning model is a LightGBM model optimized based on TPE.

16. A non-transitory computer storage medium, wherein the computer storage medium stores a computer execution instruction, and the computer execution instruction is configured to implement the method for early warning the unsafe behavior in drilling operation according to claim 2 when the computer execution instruction is executed by a processor.

\* \* \* \* \*